(12) United States Patent
Shoichet et al.

US007767656B2

(10) Patent No.: US 7,767,656 B2
(45) Date of Patent: Aug. 3, 2010

(54) BLENDS OF TEMPERATURE SENSITIVE AND ANIONIC POLYMERS FOR DRUG DELIVERY

(76) Inventors: Molly S Shoichet, 15 Austin Crescent, Toronto, Ontario (CA) M5R 3E4; Dimpy Gupta, 1 Massey, Square, Apt. #2405, Toronto, Ontario (CA) M4C 5L4; Charles H. Tator, c/o Toronto Western Hospital, Toronto, Ontario (CA) M5T 2S8

( * ) Notice: Subject to any disclaimer, the term of this patent is extended or adjusted under 35 U.S.C. 154(b) by 856 days.

(21) Appl. No.: 11/410,831

(22) Filed: Apr. 25, 2006

(65) Prior Publication Data

US 2006/0280797 A1 Dec. 14, 2006

Related U.S. Application Data

(60) Provisional application No. 60/674,299, filed on Apr. 25, 2005.

(51) Int. Cl.
*A61K 31/715* (2006.01)
*A61K 31/728* (2006.01)
*A61K 31/717* (2006.01)
*A61K 9/14* (2006.01)
*A61K 47/00* (2006.01)
*A01F 13/00* (2006.01)
*A01N 25/00* (2006.01)
*A01N 43/04* (2006.01)

(52) U.S. Cl. .................... 514/57; 514/781; 424/423; 424/433; 424/488

(58) Field of Classification Search ................ None
See application file for complete search history.

(56) References Cited

U.S. PATENT DOCUMENTS

| | | | |
|---|---|---|---|
| 4,065,578 A | 12/1977 | Reggio et al. | |
| 4,140,562 A | 2/1979 | Gualillo et al. | |
| 4,786,521 A | 11/1988 | Bennett et al. | |
| 5,153,174 A | 10/1992 | Band et al. | |
| 5,190,759 A | 3/1993 | Lindblad et al. | |
| 5,607,999 A | 3/1997 | Shimizu et al. | |
| 5,622,718 A | 4/1997 | Al-Shamkhani et al. | |
| 5,651,980 A | 7/1997 | Lanza et al. | |
| 5,997,895 A * | 12/1999 | Narotam et al. | 424/423 |
| 6,063,405 A | 5/2000 | Drizen et al. | 424/488 |
| 6,335,035 B1 | 1/2002 | Drizen et al. | 424/488 |
| 6,440,940 B1 | 8/2002 | Doyle et al. | |
| 6,548,081 B2 | 4/2003 | Sadozai et al. | |
| 6,586,493 B1 | 7/2003 | Massia et al. | 522/87 |
| 6,602,859 B2 | 8/2003 | Miyamoto et al. | |
| 6,620,927 B2 | 9/2003 | Bulpitt et al. | |
| 6,642,213 B1 | 11/2003 | Pastorello et al. | |
| 6,692,766 B1 | 2/2004 | Rubenstein et al. | 424/487 |
| 6,699,471 B2 | 3/2004 | Radice et al. | |
| 6,699,484 B2 | 3/2004 | Whitmore et al. | |
| 6,716,251 B1 | 4/2004 | Asius et al. | 623/23.58 |
| 6,723,709 B1 | 4/2004 | Pressato et al. | |
| 6,837,248 B2 | 1/2005 | Zawadzki et al. | |

FOREIGN PATENT DOCUMENTS

JP        2003342197        * 12/2003

OTHER PUBLICATIONS

Machine translation of JP2003342197 Dec. 2003.*
Prestwich et al. (Journal of Controlled Release 1998, 53, 93-103).*
Claim Amendments; Mar. 1, 2010; 9 pages.*
Kim, M.R. et al., "Temperature-responsive and degradable hyaluronic acid/pluronic composite hydrogels for controlled release of human growth hormone," *Journal of Controlled Release*, 2002, 80, 69-77.
Larson, R.G., "The rheology of dilute solutions of flexible polymers: progress and problems," *J. Rheology*, 2005, 49(1), 1-70.
Liang, H.-F. et al., "Novel method using a temperature-sensitive polymer (methylcellulose) to thermally gel aqueous alginate as a pH-Sensitive hydrogel," *Biomacromolecules*, 2004, 5, 1917-1925.
Metz, G.A.S. et al., "Efficient testing of motor function in spinal cord injured rats," *Brain Res.*, 2000, 883, 165-177.
Ohya, S. et al., "Thermoresponsive artificial extracellular matrix for tissue engineering: hyaluronic acid bioconjugated with poly(N-isopropylacrylamide) grafts," *Biomacromolecules*, 2001, 2, 856-863.
Sakiyama-Elbert, S.E. et al., "Development of fibrin derivatives for controlled release of heaparin-binding growth factors," *J. Controlled Release*, 2000, 65, 389-402.
Silver, F.H. et al., "Physical properties of hyaluronic acid and hydroxypropylmethylcellulose in solution: evaluation of coating ability," *Journal of Applied Biomaterials*, 1994, 5, 89-98.
Tate, M.C. et al., "Biocompatibility of methylcellulose-based constructs designed for intracerebral gelation following experimental traumatic brain injury," *Biomaterials*, 2001, 22, 1113-1123.
Xu, Y. et al., "Salt-assisted and salt-suppressed sol-gel transitions of methylcellulose in water," *Langmuir*, 2004, 20, 646-652.
Basso, D.M. et al., "Graded histological and locomotor outcomes after spinal cord contusion using the NYU weight-drop device versus transection," *Exp. Neurol.*, 1996, 139, 244-256.
Chenite, A. et al, "Novel injectable neutral solutions of chitosan form biodegradable gels in situ," Biomaterials, 2000, 21, 2155-2161.
Cho, K.Y. et al., "Release of ciprofloxacin from poloxamer-graft-hyaluronic acid hydrogels in vitro," International Journal of Pharmaceutics, 2003, 260, 83-91.
Hoffman, A.S., "Bioconjugates of intelligent polymers and recognition proteins for use in diagnostics and affinity separations," Clinical Chemistry, 2000, 46(9), 1478-1486.

(Continued)

*Primary Examiner*—Ernst V Arnold
(74) *Attorney, Agent, or Firm*—Woodcock Washburn, LLP

(57) ABSTRACT

A physical blend of inverse thermal gelling and shear-thinning, thixotropic polymers that has a lower gelation temperature than the thermal gelling polymer alone is provided. The blend results in an injectable hydrogel that does not flow freely at room temperature, but is injectable due to its shear-thinning properties. The thermal-gelling properties of the polymer promote a more mechanically stable gel at body temperature than at room temperature. The polymer matrix gel has inherent therapeutic benefit and can also be used as a drug delivery vehicle for localized release of therapeutic agents.

31 Claims, 15 Drawing Sheets

OTHER PUBLICATIONS

Rastello De Boisseson M, et al., Physical alginate hydrogels based on hydrophobic or dual hydrophobic/ionic interactions: bead formation, structure, and stability. J Colloid Interface Sci. May 1, 2004;273(1):131-9 [abstract only].

Leonard M, et al., Production of microspheres based on hydrophobically associating alginate derivatives by dispersion/gelation in aqueous sodium chloride solutions. J Biomed Mater Res A. Feb. 1, 2004;68(2):335-42 [abstract only].

Babak VG, et al., Hydrophobically Associating Alginate Derivatives: Surface Tension Properties of Their Mixed Aqueous Solutions with Oppositely Charged Surfactants, J of Coll and Interface Sci, 225(2), May 15, 2000 [abstract only].

Ochiai H, et al. Bottom-up synthesis of hyaluronan and its derivatives via enzymatic polymerization: direct incorporation of an amido functional group. Biomacromolecules. Mar.-Apr. 2005;6(2):1068-84 [abstract only].

Aytekin AO, et al. Role of a hyaluronic-acid derivative in preventing surgical adhesions and abscesses related to dropped bile and gallstones in an experimental model. Am J Surg. Sep. 2004;188(3):288-93 [abstract only].

Chen JH, Research of cross-linking reagent for producing hyaluronic acid derivative. Zhongguo Xiu Fu Chong Jian Wai Ke Za Zhi. Jan. 2004;18(1):70-3 [abstract only].

Manna F, et al. Comparative chemical evaluation of two commercially available derivatives of hyaluronic acid (hylaform from rooster combs and restylane from streptococcus) used for soft tissue augmentation. J Eur Acad Dermatol Venereol. Nov. 1999;13(3):183-92 [abstract only].

* cited by examiner (■) MC7% G', (◆) MC7% G", (■) MC9% G', (◆) MC9% G", (■) HAMC G', (◆) HAMC G"

(■) MC7% G', (♦) MC7% G", (■) MC9% G', (♦) MC9% G", (■) HAMC G',
(♦) HAMC G"

(♦) MC7%, (■) MC9%, (▲) HAMC (♦) MC7%, (■) MC9%, (▲) HAMC

7% MC (◆), 9% MC (■), HAMC 2%/7% (▲).

Control: Collagen

HAMC

Scale: 100μm

BLENDS OF TEMPERATURE SENSITIVE AND ANIONIC POLYMERS FOR DRUG DELIVERY

CROSS REFERENCE TO RELATED APPLICATIONS

This application claims benefit to U.S. Provisional Application Ser. No. 60/674,299, filed Apr. 25, 2005, which is incorporated herein by reference in its entirety.

FIELD OF THE INVENTION

The present invention relates to a polymer matrix comprising an inverse thermal gelling polymer and an anionic gelling polymer that exists as a solid gel. This polymer matrix has a faster gelling rate than that of either the inverse gelling polymer or the anionic polymer individually, and may be used alone or as a drug delivery vehicle for many applications. In particular, the polymer matrix can be used for localized, targeted delivery of pharmaceutical agents upon injection providing sustained release. A particularly advantageous use of this invention is in delivery of a therapeutic agent to a fluid-filled space, such as the intrathecal space, in a highly localized, targeted manner, wherein the polymer matrix-contained therapeutic agent is able to cross the blood-spinal cord barrier.

BACKGROUND OF THE INVENTION

U.S. Pat. No. 6,335,035 ('035) to Drizen, et al. is a divisional of U.S. Pat. No. 6,063,405 to Drizen et al. which teaches sustained release compositions comprising a drug dispersed within a polymer matrix, methods of producing the same and treatments with the complex. The '035 patent discloses a sustained drug delivery system, which comprises a drug dispersed within a polymer matrix solubilized or suspended in a polymer matrix. The polymer matrix is composed of a highly negatively charged polymer material selected from the group consisting of polysulfated glucosoglycans, glycoaminoglycans, mucopolysaccharides and mixtures thereof, and a nonionic polymer selected from the group consisting of carboxymethylcellulose sodium, hydroxypropylcellulose and mixtures thereof. Nonionic polymers are generally used in amounts of 0.1% to 1.0% and preferably from 0.5% to 1.0%. Nonionic polymers in amounts above 1.0% are not used as they result in the formation of a solid gel product when employed in combination with an anionic polymer.

U.S. Pat. No. 6,692,766 to Rubinstein et al. concerns a controlled release drug delivery system comprising a drug which is susceptible to enzymatic degradation by enzymes present in the intestinal tract; and a polymeric matrix which undergoes erosion in the gastrointestinal tract comprising a hydrogel-forming polymer selected from the group consisting of (a) polymers which are themselves capable of enhancing absorption of said drug across the intestinal mucosal tissues and of inhibiting degradation of said drug by intestinal enzymes; and (b) polymers which are not themselves capable of enhancing absorption of said drug across the intestinal mucosal tissues and of inhibiting degradation of said drug by intestinal enzymes.

U.S. Pat. No. 6,716,251 to Asius et al. discloses an injection implant for filling up wrinkles, thin lines, skin cracks and scars for reparative or plastic surgery, aesthetic dermatology and for filling up gums in dental treatment. The invention concerns the use of biologically absorbable polymer microspheres or microparticles suspended in a gel.

U.S. Pat. No. 6,586,493 to Massia et al. discloses hyaluronate-containing hydrogels having angiogenic and vascularizing activity and pre-gel blends for preparing the hydrogels. The hydrogels contain a cross-linked matrix of a non-angiogenic hyaluronate and a derivatived polysaccharide material, in which cross-linking is effected by free-radical polymerization.

The literature also teaches the properties of polymer matrices and their use as drug delivery vehicles (Xu et al. Langmuir, (2004) 20(3): 646-652., Liang et al. Biomacromolecules, 2004. 5(5):1917-25, Ohya et al. Biomacromolecules (2001) 2:856-863 Cho et al. International Journal of Pharmaceutics (2003) 260:83-91, Kim et al. Journal of Controlled Release (2002) 80:69-77, Tate et al. Biomaterials (2001) 22: 1113-1123, and Silver et al., Journal of Applied Biomaterials (1994) 5: 89-98).

SUMMARY OF THE INVENTION

The present invention relates to a polymer matrix which comprises: an inverse thermal gelling polymer and an anionic gelling polymer in a solid gel formulation. The polymer matrix has a faster rate of gelling than each component separately. This is because the incorporation of the anionic gelling polymer is able to decrease the gelling temperature of the inverse thermal gelling polymer. Moreover, the anionic gelling polymer possesses shear thinning properties that facilitate the return of the polymer matrix to its original viscosity and solid gel state after shearing faster than the inverse thermal gelling polymer alone. The prior art does not describe or suggest the use of a nonionic polymer at higher concentrations in combination with an anionic polymer particularly because of the tendency for such a matrix to gel. The prior art does not appear to recognize the contribution of HA or other anionic polymers to the gel formation of inverse thermal gelling polymers.

The inverse thermal gelling polymer may be selected from methylcellulose, a chitosan and β-glycerophosphate solution, collagen, tri-block copolymer of poly(ethylene glycol)-poly (lactic-co-glycolic acid)-poly(ethylene glycol), tri-block copolymer of poly(propylene glycol)-poly(ethylene glycol)-poly (propylene glycol), poly(N-isopropyl acrylamide), agarose, copolymers of poly-N-isopropylacrylamide, polysaccharides and mixtures thereof. The molecular weight of the inverse thermal gelling polymer is preferably between about 2,000 Da and about 1,000,000 Da.

The anionic gelling polymer is selected from hyaluronic acid, derivatives of hyaluronic acid, alginate, derivatives of alginate, carboxymethylcellulose, and mixtures thereof. The molecular weight of the anionic gelling polymer is preferably between about 100,000 Da and about 7,000,000 Da.

One embodiment of this invention is a blend of the inverse thermal gelling polymer methylcellulose and the anionic gelling polymer hyaluronic acid where injection of the polymer matrix alone has therapeutic benefit, particularly with respect to spinal cord injury.

Another embodiment of this invention involves the use of the polymer matrix as a delivery vehicle for a therapeutic agent. The polymer matrix formulation microencapsulates, suspends or otherwise traps the therapeutic agent such that the agent can be injected to achieve highly targeted, localized delivery. When delivered in the intrathecal space, those drugs that normally do not cross the blood-brain barrier or the blood-spinal cord barrier can be delivered. In addition, sustained release of the agent is achieved. The drug or therapeutic agent that can be delivered using this polymer matrix may be selected from a wide variety of medicaments including:

anesthetics including those used in caudal, epidural, inhalation, injectable, retrobulbar, and spinal applications, such as bupivacaine and lidocaine; analgesics, such as acetaminophen, ibuprofen, fluriprofen, ketoprofen, voltaren, phenacetin and salicylamide; anti-inflammatories selected from the group consisting of naproxen and indomethacin; antihistamines, such as chlorpheniramine maleate, phenindamine tartrate, pyrilamine maleate, doxylamine succinate, henyltoloxamine citrate, diphenhydramine hydrochloride, promethazine, brompheniramine maleate, dexbrompheniramine maleate, clemastine fumarate and triprolidine; antitussives selected from the group consisting of dextromethorphan hydrobromide and guaifenesin; expectorants such as guaifenesin; decongestants, such as phenylephrine hydrochloride, phenylpropanolamine hydrochloride, pseudoephedrine hydrochloride, ephedrine; antibiotics including amebicides, broad and medium spectrum, fungal medications, monobactams and viral agents and specifically including such as erythromycin, penicillin and cephalosporins and their derivatives; bronchodilators such as theophylline, albuterol and terbutaline; cardiovascular preparations such as diltiazem, propranolol, nifedepine and clonidine including alpha adrenoceptor agonist, alpha receptor blocking agent, alpha and beta receptor blocking agent, antiotensin converting enzyme inhibitors, beta blocking agents, calcium channel blocker, and cardiac glycosides; central nervous system drugs such as thioridazine, diazepam, meclizine, ergoloid mesylates, chlorpromazine, carbidopa and levodopa; metal salts such as potassium chloride and lithium carbonate; minerals selected from the group consisting of iron, chromium, molybdenum and potassium; immunomodulators; immunosuppressives including minocycline, cyclosporine A, and others; thyroid preparations such as synthetic thyroid hormone, and thyroxine sodium; peptide and glycoprotein hormones and analogues such as human chorionic gonadotrophin (HCG), corticotrophin, human growth hormone (HGH—Somatotrophin) and erythropoietin (EPO); steroids and hormones including ACTH, anabolics, androgen and estrogen combinations, androgens, corticoids and analgesics, estrogens, glucocorticoid, gonadotropin, gonadotropin releasing, hypocalcemic, menotropins, parathyroid, progesterone, progestogen, progestogen and estrogen combinations, somatostatin-like compounds, urofollitropin, vasopressin, methyl prednisolone, GM1 ganglioside, cAMP, and others; vitamins selected from water-soluble vitamins such as B complex, vitamin C, vitamin B12 and folic acid and veterinary formulations; growth factors such as EGF, FGF2 and neurotrophin; peptides and other protein preparations, with or without a preservative present; DNA and various forms of small interfering RNAs. The only requirement for drug selection is its solubility in an aqueous solution.

Sustained release of the therapeutic agent can be varied through modification of the polymer matrix itself. In addition, charge stabilizing factors can be added to promote interactions between the therapeutic agent and the polymer. Furthermore, the therapeutic agent can be covalently attached to the polymer to sustain its release.

BRIEF DESCRIPTION OF THE DRAWINGS

Certain embodiments of the present invention are described in greater detail with reference to the accompanying drawings.

DETAILED DESCRIPTION OF ILLUSTRATIVE EMBODIMENTS

Figure 1:
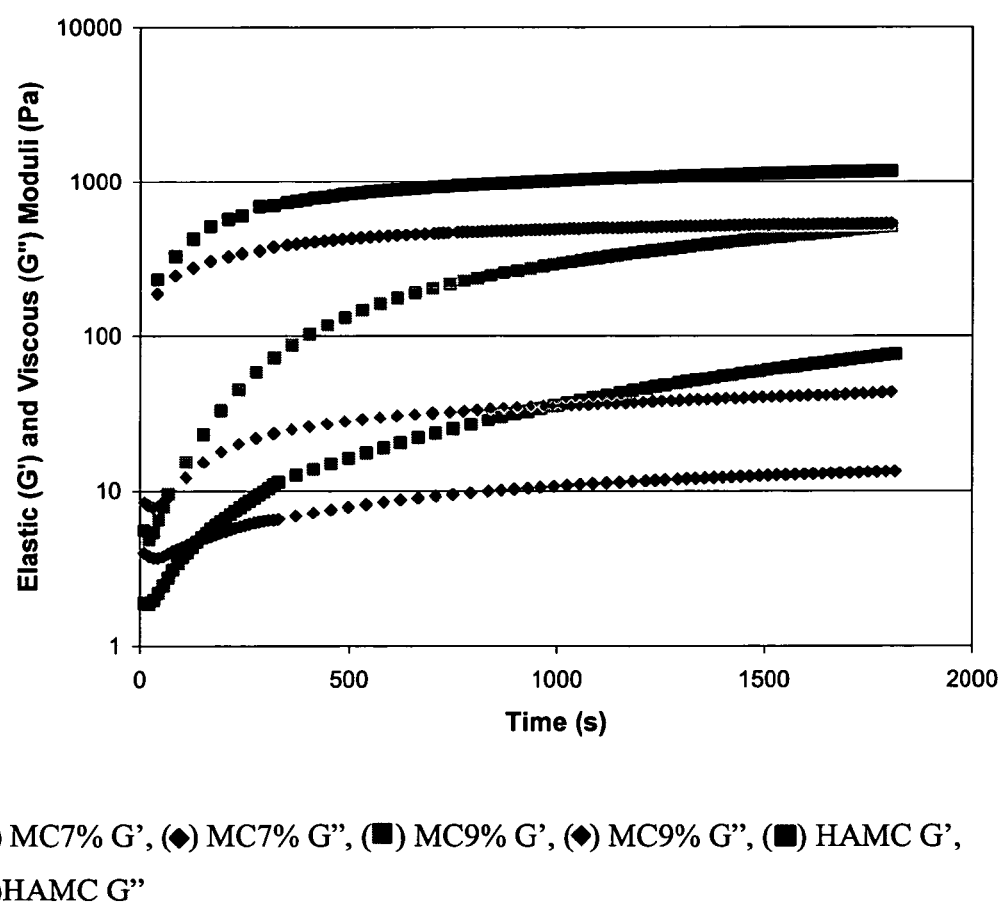
FIG. 1 shows the gelation time of injectable gels at 37° C. as determined by rheology.

The present invention may be understood more readily by reference to the following detailed description taken in connection with the accompanying figures and examples, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention.

The present invention relates to a gel solid polymer matrix comprising an inverse thermal gelling polymer and an anionic gelling polymer capable of injection to a localized site. The polymer matrix can act as a carrier for a therapeutic agent or pharmaceutical to provide sustained, controlled release of the agent in a highly targeted manner. Specifically, the invention concerns formulations of the polymer matrix, the polymer matrix as a drug delivery vehicle and use of the polymer matrix to deliver therapeutic agents to a site of injection. Sites of injection include the intrathecal space, intra-articular space, and other fluid-filled cavities as well as transdermal, oral, sub-cutaneous, intranasal, vaginal, buccal, epidural, ocular space, dental, intratumoral, intramuscular, or intravenous injectable delivery of the polymer matrix on its own or in combination with a therapeutic agent.

The polymer matrix used in this type of system must meet the following criteria:
- injectable through a fine needle which allows for a minimally invasive surgery
- fast gelling to ensure localized drug delivery at the site of injury
- degraded to avoid additional surgeries for device-removal
- subject to minimal swelling to avoid further compression of the spinal cord
- generally non-cell adhesive to limit cellular invasion and scar formation
- biocompatible to limit foreign-body reaction The gelation temperature of thermal gelling materials as well as the kinetics of gelation is concentration dependent. Immediately upon injection of a temperature sensitive polymer into a fluid filled cavity, the polymer disperses prior to gelling. The dispersion causes the gelation rate to decrease. This phenomenon also occurs with chemically cross linked gels where the kinetics are concentration dependent. To overcome this obstacle, it is necessary to have a highly viscous material so that once injected, it will not disperse and thereby suffer from a decreased gelation rate. At the same time, however, the viscous material must still be injectable and this can be achieved with the use of a shear-thinning material. Blending a highly negatively charged anionic gelling polymer with an inverse thermal gelling polymer at certain molar ratios can achieve this effect.

The anionic gelling polymer of this invention has a preferable molecular weight between about 100,000 and about 7,000,000 Da. Exemplary, non-limiting examples of anionic gelling polymers include: alginate, derivatives of alginate, carboxymethylcellulose, and mixtures thereof. Particularly preferred is hyaluronic acid (HA). HA is a linear polysaccharide composed of repeating disaccharide units of N-acetylglycosamine and D-glucoronic acid. HA is a highly viscoelastic and shear-thinning fluid that has been used for drug delivery, tissue engineering applications as well as for soft tissue augmentation. HA is known to have wound-healing effects such as anti-inflammation, as well as to minimize tissue adhesion and scar formation. It is degraded enzymatically by hyaluronidase, which can be produced by all cells. Its polymeric chains, of lengths 10-15 thousand disaccharides, form random coils with large spheroidal hydrated volumes of up to 400-500 nm in diameter. Because of the high solubility of HA in water, it must be chemically modified to form a gel. Reactions can occur at the carboxyl group, or the hydroxyl group of HA and also at the amino group once the N-acetyl group is removed. HA is injectable upon an application of force to a syringe because the shear-thinning properties of HA cause the polymer chains to straighten and align themselves permitting flow through the needle. HA then returns to its gel structure upon exiting the needle as the polymeric chains once again become entangled amongst themselves. Thus, HA is described as a shear-thinning polymer.

The inverse thermal gelling polymer of this invention is capable of gelling upon an increase in temperature. Preferably, inverse thermal gelling polymers are of a molecular weight between about 2000 and about 1,000,000 Da. Exemplary, non-limiting examples of inverse thermal gelling polymers include methylcellulose, a chitosan and $\square$-glycerophosphate solution, collagen, tri-block copolymer of poly(ethylene glycol)-poly(lactic-co-glycolic acid)-poly(ethylene glycol), tri-block copolymer of poly(propylene glycol)-poly(ethylene glycol)-poly (propylene glycol), poly(N-isopropyl acrylamide), agarose, copolymers of poly-N-isopropylacrylamide, polysaccharides and mixtures thereof. Particularly preferred is methylcellulose (MC), a carbohydrate and derivative of cellulose. MC is an example of a temperature sensitive gel, or a thermally reversible gel, that gels upon increase in temperature. When the degree of substitution of hydroxyl groups with methyl groups is between 1.4-1.9, methylcellulose has inverse thermogelling properties whereby it gels upon an increase of temperature. As the temperature increases, hydrogen bonds with the surrounding solvent break and hydrophobic junctions form to produce a gel. Methylcellulose generally forms weak gels at 37° C. when in water, but the gelation temperature can be decreased by an increase in salt concentration. This occurs because the water molecules surround the salts, effectively reducing the number of polymer-solvent interactions. Methylcellulose has previously been considered as a scaffold for experimental traumatic brain injury where in vivo tests in rats indicated biocompatibility over a span of two weeks. MC has also been used as a scaffold in the peripheral nervous system for nerve regeneration with promising results, without any adverse pathological reactions over 8 weeks. Although it is not found to degrade enzymatically, the weak gel structure does dissolve at 37° C. and swells minimally.

To take advantage of the thermal gelling properties of MC and the shear-thinning properties of HA, MC and HA were blended. The combination of an aqueous solution of MC and lyophilized HA results in dispersal of HA within the solution. The resulting polymer matrix is a fast-gelling polymer and is referred to as HAMC. Methods of blending polymer matrices for drug delivery are well known. In general, methods to prepare HAMC involve preparation of a sterile solution of MC in a buffered salt solution, which was cooled to 4° C. prior to the addition of sterile, lyophilized HA which dissolved over time. Because of the high viscosity of this material prior to gelation, HAMC does not flow significantly at room temperature. This allows the polymer blend to maintain some structure as it gels. It is expected that since HA strongly interacts with the solvent, the presence of HA in a MC solution likely dehydrates the MC, similar to the effect of salt on MC gelation, effectively decreasing the gelation temperature. Hence, HA also functions to lower the gelation temperature of MC.

HAMC is unique amongst physical gelling polymers in its ability to return to its initial viscosity more rapidly. Typically, physical gelling polymers undergo a phase transition from a solution to a gel after injection whereas HAMC is a gel both prior to and following injection. The shear thinning properties of HA enable the HAMC gel to be injectable while the thermal gelling properties of MC aid in returning the HAMC to a gel following injection. The properties of the gel are highly sensitive to the amount of HA, and altering the concentration of HA would be expected to affect the injectability of the polymer matrix and the gelation rate. For example, higher molecular weights of HA are likely to dissolve more slowly, and perhaps have improved shear thinning properties. Varying the concentrations of the individual polymers as well as the use of polymers of different molecular weights enhances the properties of the polymer matrix for injectable delivery.

The polymer matrix of this invention can be used to target delivery of a pharmaceutical agent by means of injection. It is well known in the art that pharmaceutical agents can be loaded into polymer matrices with high loading efficiency while retaining the agent's bioactivity. Common methods include imbibing the pharmaceutical agents into pre-formed matrices or incorporating the pharmaceutical agent in the preparation of the polymer matrix itself (Liang et al. Biomacromolecules 5:1917-1925 (2004), Cho et al. Int. J. Pharmaceutics 260:83-91 (2003), Kim et al. J. Controlled Release 80:69-77 (2002). For HAMC, both methods will work. Preferably, the therapeutic agent(s), protein(s) or peptide(s) will have some solubility in the MC solution prior to the addition of HA. The solution is maintained overnight to allow the HA to completely dissolve in the solution. The injectable polymer matrix of this invention provides the following advantages: localized drug release, improved drug distribution, and controlled release rates. Localised drug release at the site of injury enhances therapeutic efficacy, thereby minimizing the risks of systemic toxicity and side effects. Since less drug is lost systemically, localized release also allows for lower doses of drug to be released for therapeutic efficacy. Drug distribution is improved through the localised delivery and by sustained release rates.

Non-limiting examples of pharmaceutical agents deliverable by means of this polymer matrix include: anesthetics including those used in caudal, epidural, inhalation, injectable, retrobulbar, and spinal applications, such as bupivacaine and lidocaine; analgesics, such as acetaminophen, ibuprofen, fluriprofen, ketoprofen, voltaren, phenacetin and salicylamide; anti-inflammatories selected from the group consisting of naproxen and indomethacin; antihistamines, such as chlorpheniramine maleate, phenindamine tartrate, pyrilamine maleate, doxylamine succinate, henyltoloxamine citrate, diphenhydramine hydrochloride, promethazine, brompheniramine maleate, dexbrompheniramine maleate, clemastine fumarate and triprolidine; antitussives selected from the group consisting of dextromethorphan hydrobromide and guaifenesin; expectorants such as guaifenesin; decongestants, such as phenylephrine hydrochloride, phenylpropanolamine hydrochloride, pseudoephedrine hydrochloride, ephedrine; antibiotics including amebicides, broad and medium spectrum, fungal medications, monobactams and viral agents and specifically including such as erythromycin, penicillin and cephalosporins and their derivatives; bronchodilators such as theophylline, albuterol and terbutaline; cardiovascular preparations such as diltiazem, propranolol, nifedepine and clonidine including alpha adrenoceptor agonist, alpha receptor blocking agent, alpha and beta receptor blocking agent, antiotensin converting enzyme inhibitors, beta blocking agents, calcium channel blocker, and cardiac glycosides; central nervous system drugs such as thioridazine, diazepam, meclizine, ergoloid mesylates, chlorpromazine, carbidopa and levodopa; metal salts such as potassium chloride and lithium carbonate; minerals selected from the group consisting of iron, chromium, molybdenum and potassium; immunomodulators; immunosuppressives including minocycline, cyclosporine A, and others; thyroid preparations such as synthetic thyroid hormone, and thyroxine sodium; peptide and glycoprotein hormones and analogues such as human chorionic gonadotrophin (HCG), corticotrophin, human growth hormone (HGH—Somatotrophin) and erythropoietin (EPO); steroids and hormones including ACTH, anabolics, androgen and estrogen combinations, androgens, corticoids and analgesics, estrogens, glucocorticoid, gonadotropin, gonadotropin releasing, hypocalcemic, menotropins, parathyroid, progesterone, progestogen, progestogen and estrogen combinations, somatostatin-like compounds, urofollitropin, vasopressin, methyl prednisolone, GM1 ganglioside, cAMP and others; and vitamins selected from water-soluble vitamins such as B complex, vitamin C, vitamin B12 and folic acid and veterinary formulations as well as growth factors such as EGF, FGF2 and neurotrophin, peptides and peptide mimetics; as well as DNA and various forms of small interfering RNA.

The drug delivery synergistic polymer matrix of this invention has multiple applications and may be delivered via injection, transdermal, oral, sub-cutaneous, intranasal, vaginal, buccal, intrathecal, epidural, ocular space, dental, intratumoral, intramuscular, intraarticular, and intraveneously. The drug delivery synergistic polymer matrix is designed for delivery into a fluid-filled (or partially-filled) cavity. These include all cavities throughout the body, including but not limited to the intrathecal space, the intra-articular cavity, among others.

The polymer matrix components can be modified to alter the degradation rate of the matrix and, hence, affect the rate of release of the pharmaceutical agent from the matrix. One such modification involves addition of salts to alter the pH. Since the charge of the anionic gelling polymer causes its viscosity to be pH sensitive, it is possible that the polymer matrix blend is also pH sensitive. The pH can be varied to control properties such as formulation for delivery or processing. A pH-sensitive hydrogel composed of methylcellulose and alginate was previously demonstrated by Liang et al. (Biomacromolecules 5:1917-1925, 2004) to be capable of increased load release at a higher pH (pH 7.4) compared to a lower pH (pH 1.2). Blending of the polymer matrix with a salt could be performed to achieve a pH-dependent delivery vehicle.

Another alternative to creating a more stable gel for slower degradation is to functionalize the polymers with thiol groups and acrylate groups. The polymer matrix is injected and gels quickly at the site of injection because, at physiological conditions, a Michael-type addition reaction occurs between the polymer end terminated with thiol and the polymer terminated with acrylate chains. This technique results in a product that is fast gelling with a high degree of gel strength, achieved as a result of linking multiple crosslinked polymers. For example, using a methacrylated polymer, such as methacrylated dextran, and a thiol conjugated polymer, such as PEG-dithiol or a peptide-dithiol, a crosslinked dextran gel can be achieved. Using a specific amino acid sequence that is enzymatically cleaved, a degradable, injectable crosslinked polysaccharide gel can be synthesized.

Another method of controlling degradation rates is to increase the hydrophobicity of HA, which helps to maintain the integrity of gel through the formation of more hydrophobic junctions resulting in less water penetration. To render HA more hydrophobic, the reactive functional groups, hydroxyl or carboxyl, can be modified with hydrophobic molecules. For example, it is possible to modify the carboxyl group of HA with acetic hydrazide using standard coupling agents, such as carbodiimides like EDC. It should be noted that the carboxyl group is important for the highly viscous nature of the polymer matrix.

In order to further enhance sustained release of the pharmaceutical agent from the polymer matrix, the agent can be encapsulated into nanoparticles, microparticles or liposomes prior to dispersion into the polymer matrix. The nanoparticles, microparticles or liposomes encapsulate therapeutic molecules for release in a controlled manner.

Another means to enhance sustained release of the pharmaceutical agent is to take advantage of ionic interactions between the agent and the polymer. The highly negatively charged anionic gelling polymer engages in ionic interactions with positively charged molecules. In cases where there is no significant drug-polymer interaction, or the charges are the same such that there are no attractive forces, the charge can be modified with the use of charged stabilizers. Cationic particles or a mixture of cationic and anionic particles are used within the anionic gelling polymer to prevent the particles from dispersing away from the gel, as well as to promote increased gel strength through ionic crosslinks. Methods for incorporating cationic or cationic/anionic charge stabilizers into pharmaceutical compositions may be employed and are known to those of skill in the art. Examples are described in Sakiyama et al. (J. Controlled Release 65:389-402, 2000).

Another alternative to further controlling drug release is by tethering or covalently bonding the pharmaceutical agent to the polymer. The agent releases from the polymer matrix upon breakage of the covalent bond or upon dissolution of the chain from the polymer matrix network. Methods of covalently bonding pharmaceutical agents to polymers may be employed and are known to those of skill in the art. Examples are described in Hoffman et al. (Clinical Chemistry 46(9):1478-1486).

Although alginate also has carboxyl groups and is also shear thinning, it does interact with an aqueous solvent as much as HA, likely because the carboxyl groups of alginate fall on the same side of the sugar chain, whereas in HA, the carboxyl groups are on opposite sides of the sugar chain. This permits the HA carboxyl groups to interact with water on both sides of the sugar chain compared to alginate. The fact that both carboxyl groups occur on the same side of the sugar chain in alginate is what allows the alginate to form a gel with calcium ions by forming an egg-box-like structure. Despite the differences between HA and alginate with respect to solvent interaction, both alginate and HA, as well as their derivatives, can be used as the anionic polymer to achieve similar effects on the inverse thermal gelling polymer.

Chitosan, an amino-polysaccharide, is another example of an inverse thermal gelling polymer that can be used in the polymer matrix. It is obtained by the alkaline deacetylation of chitin. Chitosan is both biocompatible and biodegradable and has inherent wound healing properties, in addition to a wide range of applications in drug delivery and tissue engineering. Chitin and chitosan are generally found as copolymers, and it is the chitin segments that are enzymatically degradable by lysozyme. It is a cationic polymer which is soluble in acidic conditions. Recently, Chenite et al. (Biomaterials 21:2155-2161, 2000) developed a thermogelling polymer by mixing $\beta$-glycerophosphate ($\square$-GP) into a chitosan solution. Chitosan/$\beta$-GP gels upon an increase in temperature where the gelation temperature is affected by both pH and $\beta$-GP concentration. The negatively charged $\beta$-GP molecules are attracted to the positively charged amine groups of chitosan, preventing chitosan from aggregating and precipitating at physiological pH. Upon an increase in temperature, a gel is formed because of the formation of physical junction zones which occur when hydrophobic and hydrogen bonding forces outweigh the interchain electrostatic repulsion forces.

EXAMPLES

The present invention is further defined in the following Examples. It should be understood that these examples, while indicating preferred embodiments of the invention, are given by way of illustration only, and should not be construed as limiting the appended claims From the above discussion and these examples, one skilled in the art can ascertain the essential characteristics of this invention, and without departing from the spirit and scope thereof, can make various changes and modifications of the invention to adapt it to various usages and conditions.

Example 1

I. Blend of 2% Hyaluronic Acid and 7% Methylcellulose

The polymer matrix components were sterilized as indicated and produced under sterile conditions. Methylcellulose (MC) A15 PREM LV (Dow Chemical) was autoclaved for 20 minutes at 120° C. To produce 10 ml of a 7% methylcellulose solution, 4 ml of sterile-filtered artificial cerebrospinal fluid (aCSF)(148 mM NaCl, 3 mM KCl, 0.8 mM $MgCl_2$, 1.4 mM $CaCl_2$, 1.5 mM $Na_2HPO_4$, 0.2 mM $NaH_2PO_4$, 0.1 mg/ml bovine serum albumin) was heated to 90° C. and mixed with 0.7 g MC powder until all polymer particles were wetted. The remaining 5.3 ml aCSF was added cold and the mixture shaken in an ice bath for at least 30 minutes.

Hyaluronic acid (HA) (MW 1500000, Novamatrix) was sterilized by filtering a 0.1% HA solution in Millipore distilled water ($ddH_2O$) through a 0.22 µm PES filter (Nalgene). The solution was then lyophilized under sterile conditions by covering falcon tubes with nylon 0.2 µm filters (Millipore).

HAMC is a physical blend of 2% HA and 7% MC in aCSF. To produce HAMC, the sterilized lyophilized HA powder was added to the 7% MC solution and vortexed. The HA was allowed to dissolve into the solution overnight at 4° C.

II. Measurement of Gelation Rates of HA, MC and HAMC

HA, MC and HAMC solutions were evaluated for injectability. HA solutions prepared in artificial cerebral spinal fluid (aCSF) up to concentrations of 5% were injectable through a 30 G needle and concentrations greater than 2% were fast-gelling when the material was injected in to an empty microfuge tube. An inverted tube test was used to assess gelation. Briefly, microfuge tubes were filled with aCSF and equilibrated to 37° C. The HA polymer solution was injected into the tube and incubated at 37° C. Tubes were inverted at 2, 5, 10, 15 and 20 minute intervals to observe if the gel flowed. When injected in aCSF, HA polymers immediately swelled and dissolved in the surrounding solution. Thus, HA on its own does not meet the requirements of a fast gelling polymer in a solution. A 7% MC solution was tested as a potential injectable gel. An inverted tube test revealed the time required for the gel not to flow (the gelation time) to be 20 minutes. Thus, MC is considered to be relatively slow gelling. Using the inverted tube test described above, HAMC was found to gel faster than MC alone: 2 minutes for HAMC versus 20 minutes for MC.

Gelation time was also determined using a rheometer to measure the time at which the elastic modulus (G') of a material is equal to the viscous modulus (G"). This is referred to as the Winter and Chambon criterion. Oscillation experiments were performed at an angular frequency of 1 Hz, which mimics physiological conditions of the pulsatile CSF flow in humans. Using a rheometer to measure elastic modulus and viscous modulus as a function of temperature, an amplitude sweep was performed on the HAMC polymer matrix to confirm that the frequency and strain were within the linear viscoelastic region. FIG. 1 shows the gelation times of 7% MC, 9% MC, and HAMC (2% HA/7% MC) at 37° C. and a frequency of 1 Hz. HAMC is fast gelling and is found to be a gel even before the first measurement is taken. HAMC was found to gel in less time than MC alone. However, it is not possible to directly compare the results of the inverted tube test (which was done in the presence of an aqueous solution to mimic a fluid-filled cavity) and the rheology assay (which did not mimic gelation into a fluid-filled cavity which is an intended application site). MC had a very short gelation time as measured by the rheometer, but took much longer to gel by the inverted tube test which is a biomimetic environment. Had the gelation temperature been the only factor affecting the gelation rate, the gelation time for HAMC and MC would have been more similar by the inverted tube test as it was on the rheometer. Since this was not the case, this indicates that gelation temperature alone is not a sufficient indication of the gelation rate in a fluid cavity and suggests that the viscosity of the gel, and the ability of the gel to return to its original state after shear are also important factors. Thus, gelation time alone is not indicative of gelation in a fluid-filled cavity and gelation temperature alone is not a good predictor of gelation time.

III. Evaluation of the Thixotropic Property of HA, MC and HAMC

In order to understand why HAMC is faster gelling than MC alone, the gelation temperature and thixotropic property of the gels were investigated. Each of these properties is known to contribute to the gelling mechanisms of the gel based on the properties for the individual components, MC and HA, respectively.

Figure 2:
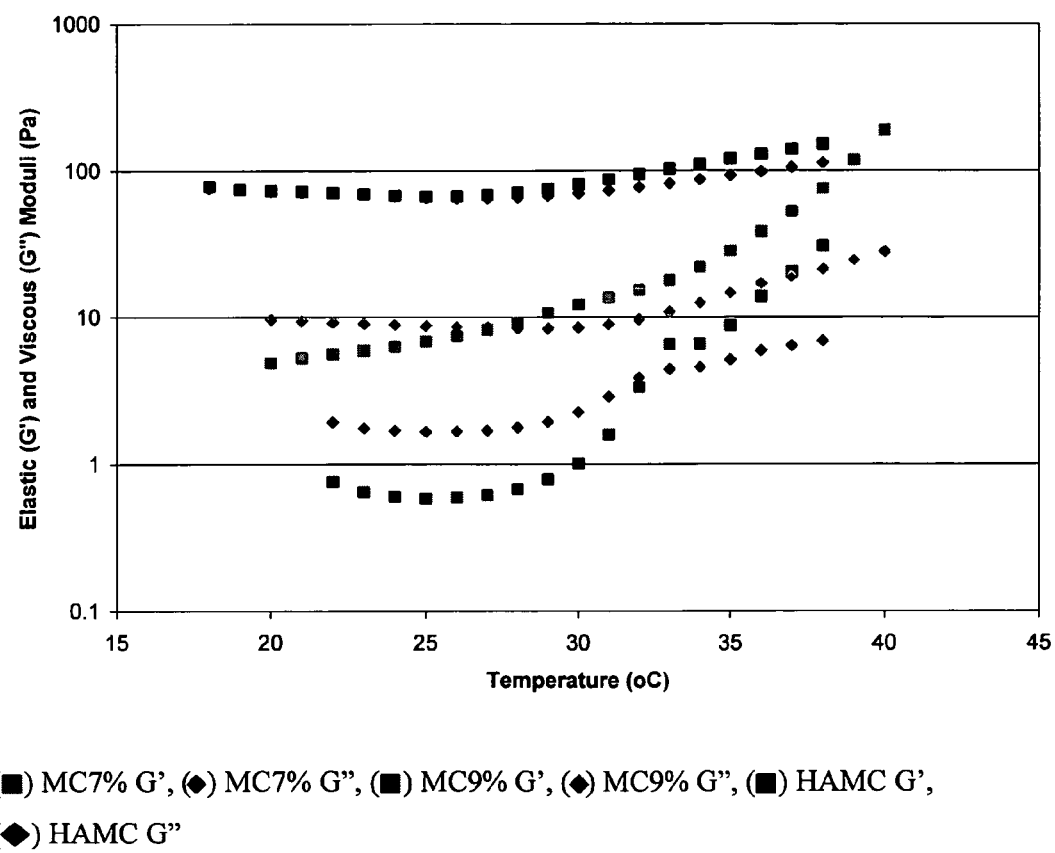
FIG. 2 shows the elastic and viscous moduli of injectable gels at 1 Hz using a rheometer with a cone and plate geometry.

The gelation temperature of the materials can be determined similarly to the method used to measure the gelation time of materials. Rather than simply measuring the moduli as a function of time, the moduli are measured as a function of temperature. As shown in FIG. 2, both 7% MC and 9% MC start as solutions and gels upon an increase in temperature as indicated by G" greater than G' at lower temperatures and vice versa (G' is greater than G") at higher temperatures. The gelation temperature for 7% MC is 32° C. while that of the more highly concentrated 9% MC is 27° C. This implies that more highly concentrated solutions are able to gel faster because of the lower gelation temperature. For HAMC, the gelation point starts at 18° C. since G' is equal to G" for a range of temperatures. As the temperature increases, G' is greater than G" indicating strengthening of the gel.

Figure 3:
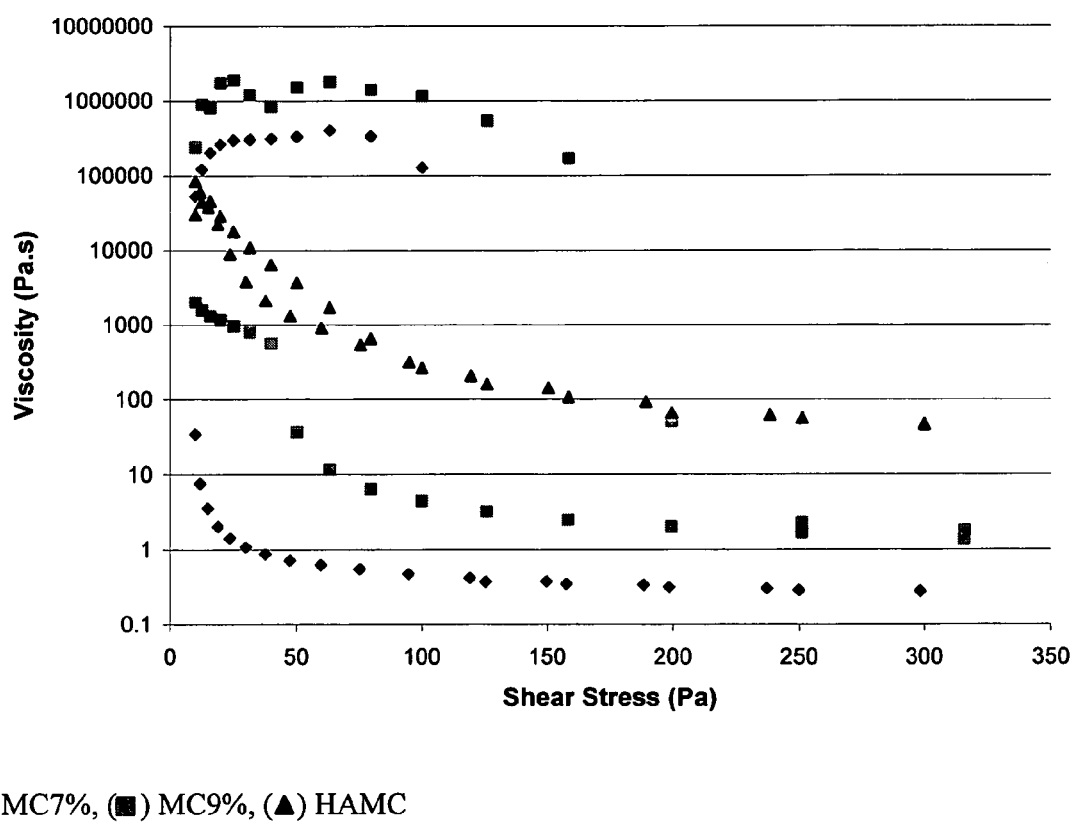
FIG. 3 shows the thixotropic loop of injectable gels at 37° C. using a rheometer with a cone and plate geometry.

Blends are composed of thermal gelling MC, and shear thinning HA. Accordingly, the gelling mechanism of the blends is based on both temperature and thixotropy. A qualitative measure of a polymer's ability to recoil and recover from a deformation has been described (reviewed in Larson R G, J. Rheology 49:1-70, 2005). With shear thinning polymers, the viscosity drops upon increasing shear and the viscosity will increase upon removal of the shearing force. However, the rate at which materials recover from the shearing force varies, based on its thixotropic loop, and this can be seen by measuring the viscosity of materials where the shear stress is increased, then decreased. The larger the area between the increasing and decreasing curves, the more time it takes for the material to recoil back to its original form. FIG. 3 is a plot of the gel viscosity as a function of the shear stress increasing, and decreasing. It is observed that the area between the curves generated for HAMC is smaller than the area generated for either of 7% MC or 9% MC, indicating that HAMC can recover from deformation much faster than MC alone.

IV. Evaluation of Degradation of the Polymer Matrix

To eliminate the need of a second surgery for the purpose of removing the drug delivery device, the injectable gel must be degradable. Moreover, polymer degradation can be used to aid with the control of drug release. It is thus desirable to develop a class of inverse thermal gelling, shear thinning polymers with varied degradation rates.

Figure 4:
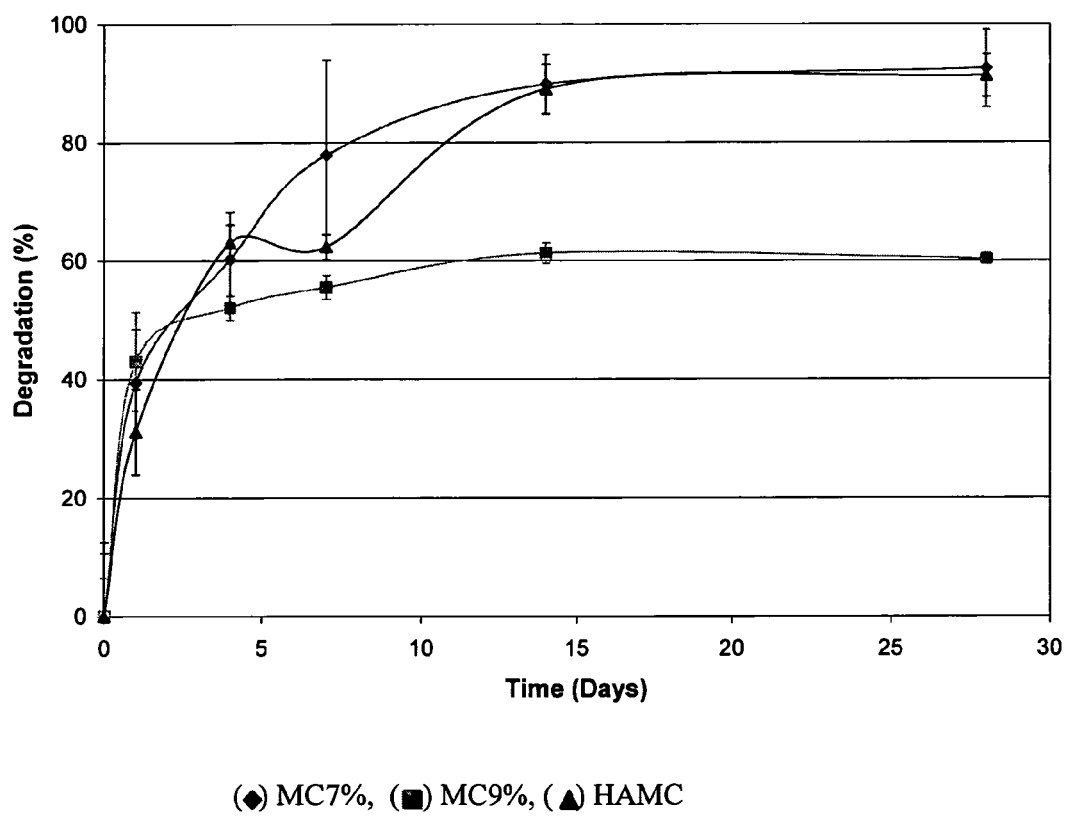
FIG. 4 shows the in vitro degradation in aCSF without hyaluronidase (HAase) of MC7%, MC9%, HAMC determined by change of dry mass over time.

Degradation and swelling of the gels were measured in vitro by quantification of the changes in wet gel weight and dry polymer weight of the material over time. As seen in FIG. 4, 7% MC and HAMC have similar degradation profiles, where 60% of the polymer matrix degrades within the first 4 days, after which the rate of degradation slows for the remainder of the 28 day study.

V. Evaluation of Polymer Matrix Swelling

Figure 5:
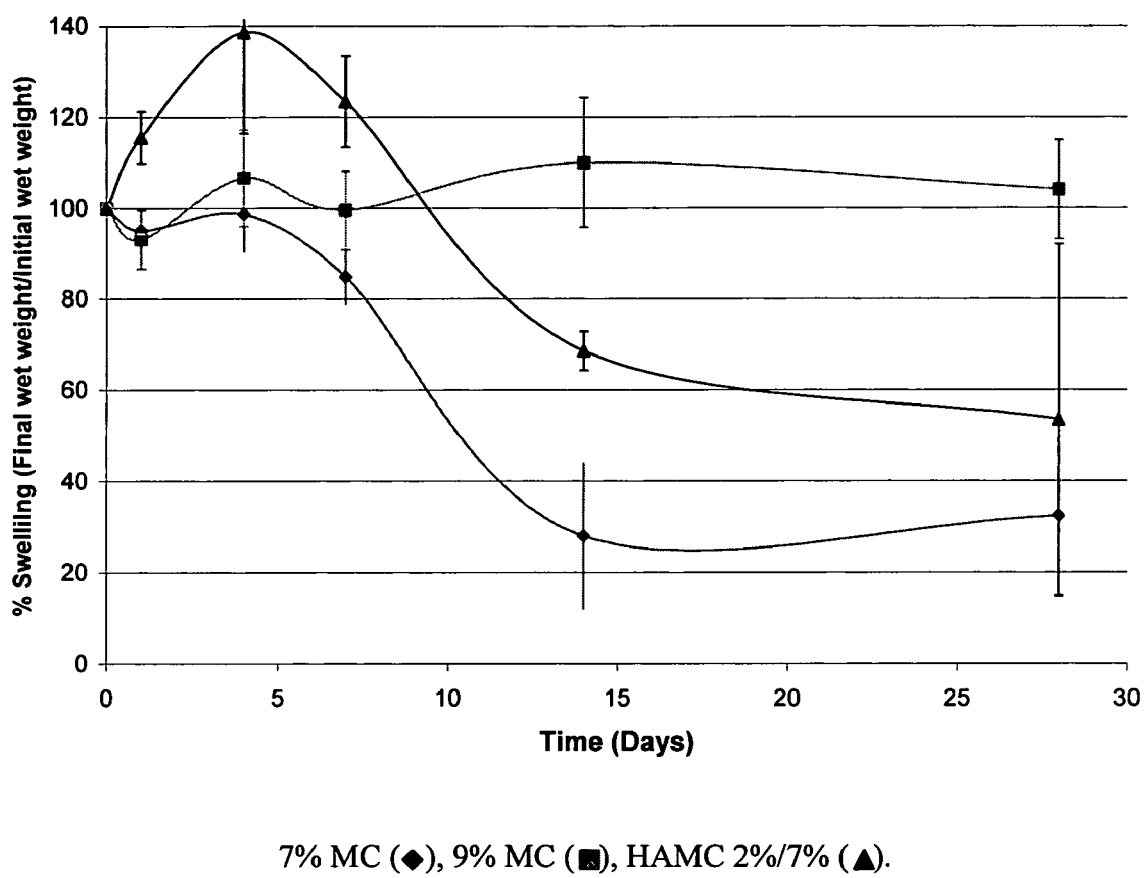
FIG. 5 shows in vitro swelling of 7% MC, 9% MC, HAMC 2%/7%.

Polymer swelling should be at a minimum to avoid further compression of the spinal cord. Polymer swelling can be calculated by the change in gel weight as a function of time as plotted in FIG. 5. According to this figure, MC and HAMC swelled a maximum of 10%-30% over its initial volume by day 7, after which point the gel weight decreases. This time period corresponds to the observed change in the rate of degradation indicated in FIG. 4; hence, swelling occurs during the fast period of degradation.

VI. Evaluation of Polymer Matrix Adhesion to Cells

Figure 6:
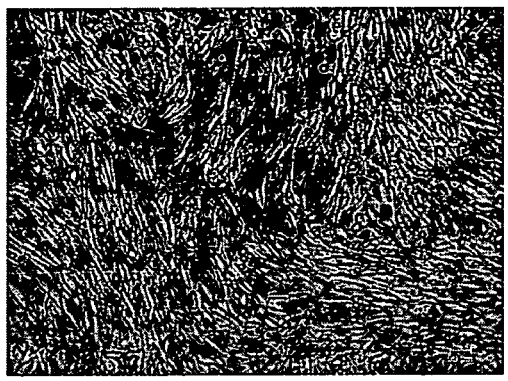
FIG. 6 shows 3T3 cells (a fibroblast cell line) that adhere to positive controls, collagen, but not to HAMC gels as determined under the light microscope.
Figure 6:
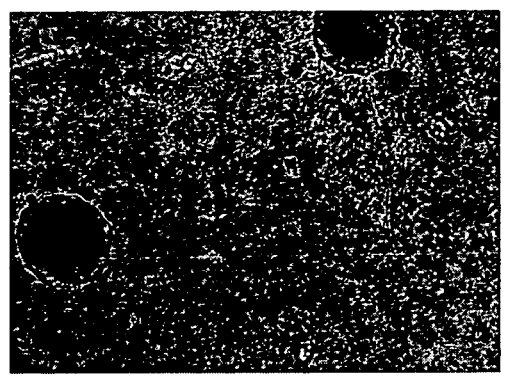

It is desirable for the injectable gel to be non-cell adhesive since an adhesive biomaterial can promote cell invasion within the matrix and scar formation; both have serious clinical complications when it occurs in the subarachnoid space. To test for cell adhesion, 3T3 fibroblast cells were cultured on each of HAMC and on collagen, a control gel. When cells adhere to the gel, the cellular morphology changes and the cells become elongated. As seen in FIG. 6, cells cultured on HAMC (FIG. 6B) prefer to adhere to each other and form clusters as opposed to adhering to the gel surface whereas cells cultured on control collagen gels adhere to the gel (FIG. 6A). This indicates that the gel is non-adhesive to fibroblast cells.

VII. Evaluation of EPO Delivery by HAMC

Figure 7:
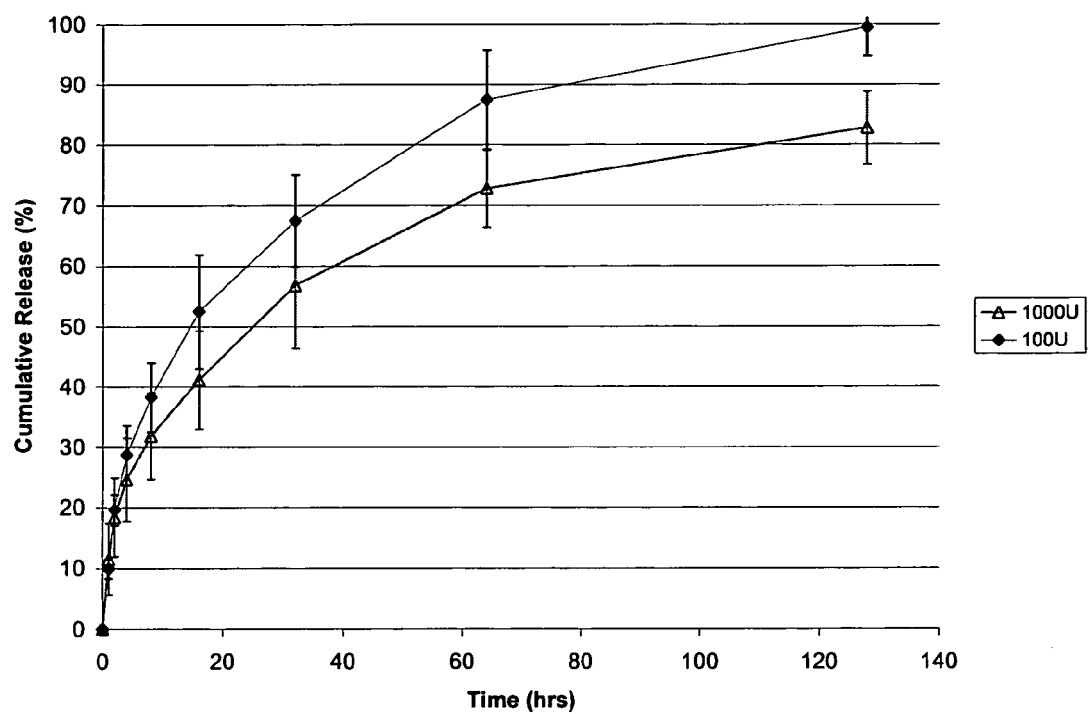
FIG. 7 shows cumulative release of EPO from HAMC 2%/7% in vitro. Two different doses of EPO (100U, 1000U) were evaluated.

EPO release from HAMC was studied. Two different doses of EPO (100U/100 μl of HAMC and 1000U/100 μl of HAMC) were evaluated for drug release fro the polymer matrix. Release samples were collected over 128 hrs and EPO concentrations were measured using enzyme-linked immunosorbent assay (ELISA). FIG. 7 shows cumulative EPO release as a percentage of the protein loaded onto HAMC. The majority of EPO was found to release from HAMC within the first 64 hours.

Figure 8:
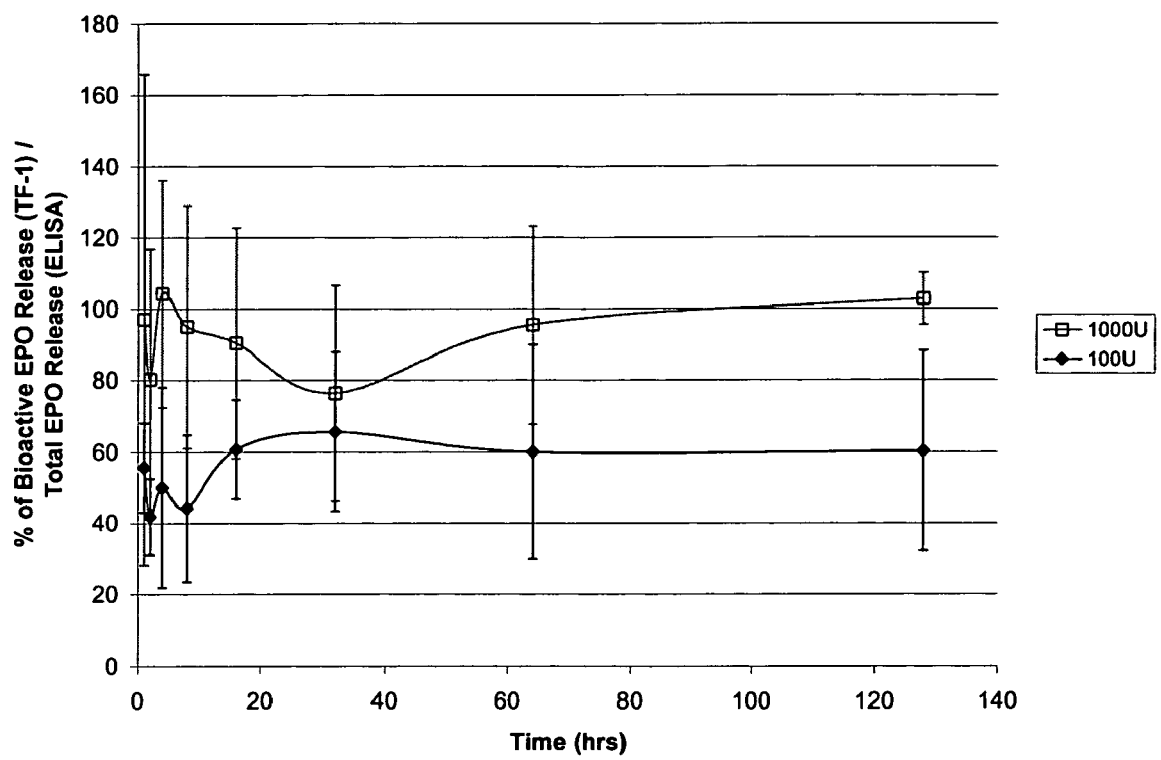
FIG. 8 shows percent of EPO release measured from HAMC in vitro using TF-1 cell assay/EPO release measured using ELISA. Two different doses of EPO (100U, 1000U) were evaluated.

To ensure the EPO released from HAMC retained its bioactivity, a cellular assay was performed for all EPO samples collected during the EPO release study. TF-1 cells are known to proliferate in the presence of EPO., Thus, cell concentrations following exposure to HAMC-EPO were measured using an MTS assay. Using the calibration curve generated, EPO release based on the cellular assay was calculated. FIG. 8 is a plot of cumulative release of EPO from HAMC as determined by a TF-1 cell proliferation assay. Briefly, the number of cells counted was divided by the cumulative release measured using ELISA. Values of 100% indicate that both assays measure the same EPO concentration, while 0% indicates that the EPO is non-bioactive. All release samples were found to have significantly higher UV absorbance values compared to control aCSF ($p<0.05$). It is observed that mean values are approximately 80-100% for the higher EPO dose samples, and approximately 40-60% for the lower EPO dose samples. This is likely due to activity loss that occurred during the freeze-thaw cycle, since a minimum EPO concentration of 250 U/ml is recommended for storing EPO. Release samples of the lower dose were below this concentration; therefore bioactivity loss is likely due to storage techniques after the release study was completed.

VIII. Evaluation of Delivery of Alkaline Phosphatase by HAMC

Figure 9:
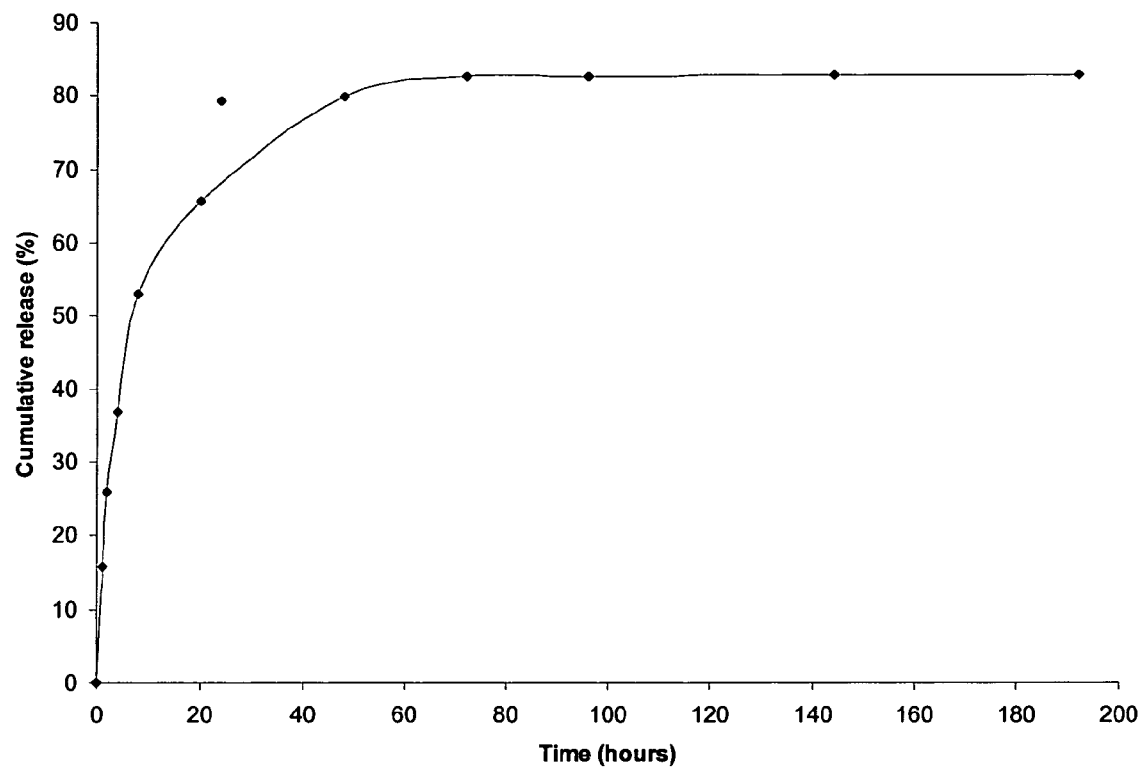
FIG. 9 is a graph of the cumulative release of alkaline phosphatase from HAMC in vitro over a period of time.
Figure 10:
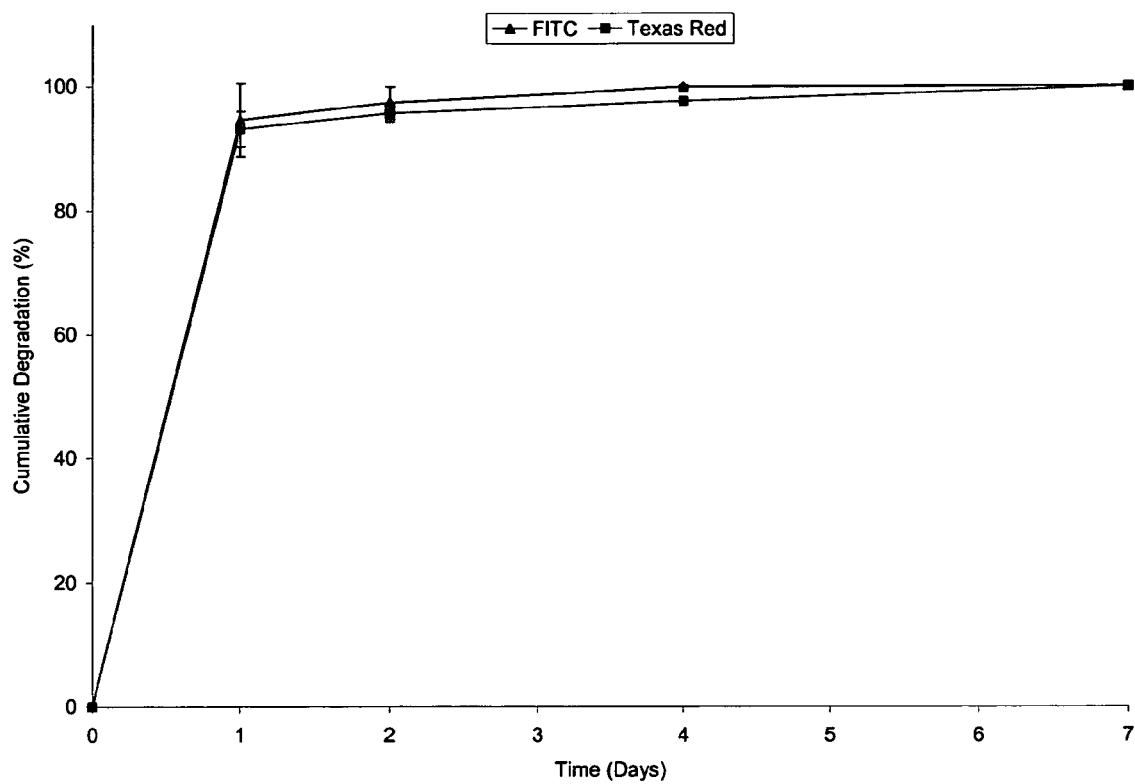
FIG. 10 is a graph of the cumulative in vivo degradation of HA (FITC labeled) and MC (Texas Red labeled) in the intrathecal space of Sprague Dawley rats, measured as a function of remaining fluorescence intensity against days post-surgery.

The release of a large enzyme molecule, alkaline phosphatase, from HAMC was also studied. FIG. 9 shows the release of alkaline phosphatase as a percentage of enzyme loaded. The majority of alkaline phosphatase was released within the first 24 hours. This shows that large, biologically active molecules can be locally delivered from HAMC, over a prolonged period.

Example 2

I. Application of HAMC for Intrathecal Injection

The drug delivery synergistic polymer matrix in Example 1 has been used for injection into the intrathecal space using a 30 G needle in Sprague-Dawley rats. A laminectomy was performed at the T2-T3 spinal level and 10 µl of sterile HAMC injected into the SAS using an anterior chamber cannula (BD Visitec). The needle is a 30 G needle, 22 mm long with a 45° angle blunt tip 4 mm from the end. The dura matter overlying the left dorsal rootlets was lifted with forceps (Dumont biologic tip, #5, FST) and punctured with a sharp 30 G needle at T3. The cannula was inserted through the dural opening and 10 µl of HAMC was injected rostrally using a 1 ml Luer-loc syringe (BD Biosciences). The cannula was maintained intrathecally for an additional minute to prevent backflow. After injection, the animals were sutured.

Twenty eight female Sprague Dawley rats were used to assess the effects of HAMC on behavior, histology and immunohistochemistry. Six animals were left uninjured and injected with 10 µl HAMC. Another 6 were left uninjured and injected with the sham 10 µl aCSF. Eight animals were injured with a 35 g clip as described in Section 2.8 and injected with HAMC, while the other 8 were also injured and injected with aCSF. Urinary tract infections were treated with subcutaneous ampicillin. The bladders of spinal cord injured (SCI) animals were manually expressed three times per day until bladder function was regained. Rats used for studying degradation were sacrificed at 0, 1, 2, 4, and 7 days and spinal cords were harvested and cryopreserved. Two uninjured animals injected with HAMC and 2 uninjured animals injected with aCSF were sacrificed at 3 days, while all others were sacrificed 28 days after surgery and perfused with 10% neutral-buffered formalin intra-cardially. Spinal cords were harvested and post-fixed in formalin. Cords were then processed and embedded in paraffin blocks.

II. Evaluation of HAMC Degradation In Vivo

Degradation of HAMC was observed in vivo by labeling HA with a FITC fluorescent tag and MC with a Texas Red fluorescent tag. Fluorescence was monitored over 1 week, and both HA and MC followed a similar degradation pattern, where both HA and MC mainly degraded within 48 hours. The degradation could be occurring from CSF fluid flow clearing the HAMC or via HAase enzymatic degradation. This shows that HAMC could be used for localized delivery of small or large molecules within the intrathecal space, and would allow for short term release of drugs. However, slight alterations of either HA or MC chains presents the potential for longer degradation and hence extended release of therapeutic agents.

III. Assessment of Effects of HAMC on Functional Behavior in Laminectomized Rats Functional behavior was assessed using the Beattie, Basso, Bresnahan (BBB) scale (Basso et al., Exp Neurol 139(2):244-256, 1996), a 21-point scale that ranks no locomotion as 0 points and normal gait as 21 points. Each hind limb was ranked by two blinded observers. Behavior was found to not worsen with the injection of HAMC.

Figure 11:
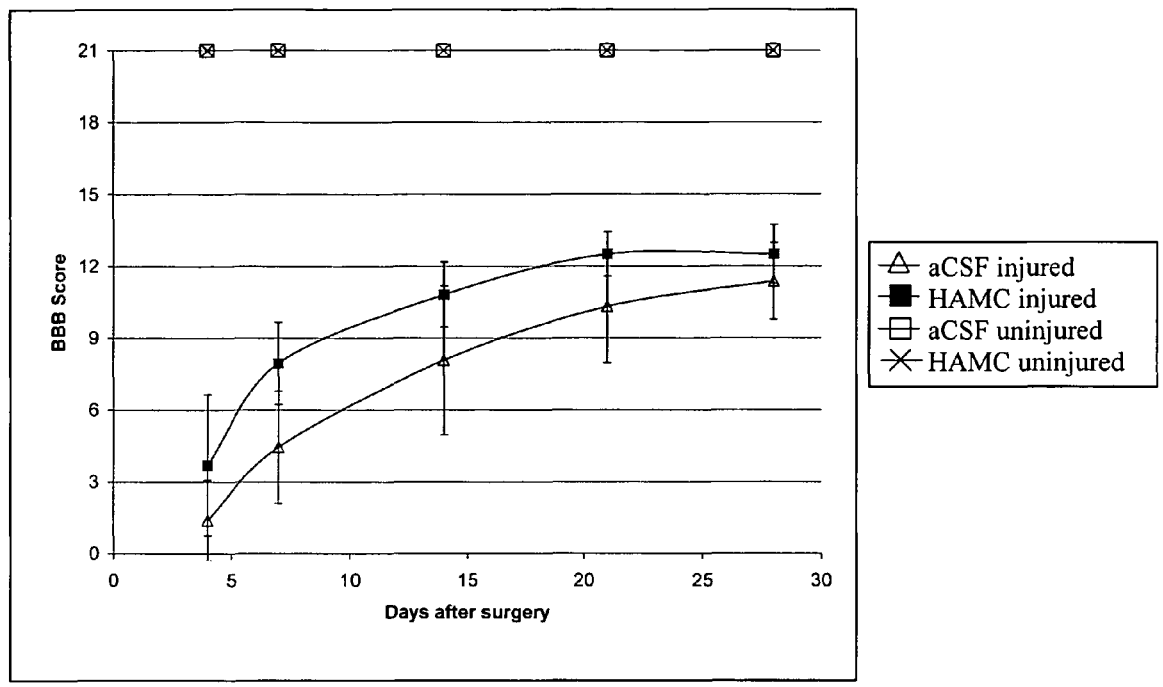
FIG. 11 is a graph of the results of BBB scores for injured and uninjured rats injected with HAMC or aCSF measured against days post-surgery.
Figure 12:
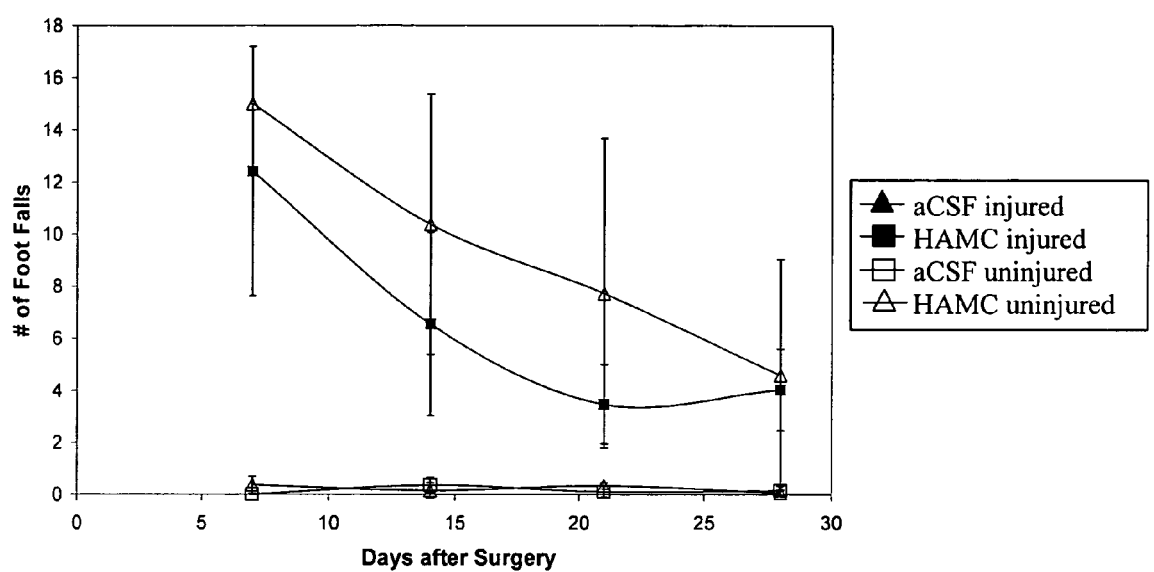
FIG. 12 is a graph of the results of grid walking scores for injured (laminectomized) and uninjured rats injected with HAMC or aCSF, measured in days post-surgery.

Limb placement and motor control were assessed by grid walk as described by Metz et al. (Brain Res 883(2):165-177, 2000). Gridwalk results confirm the conclusion that HAMC injection does not affect functional behavior. In fact, for each of the BBB and grid walk functional behavior tests, rats injected with HAMC tended to show better functional recovery than those injected with aCSF, which can be seen from FIGS. 11 and 12. With regard to FIG. 11, Day 7 data for HAMC vs. aCSF in injured animals are statistically different (n=6, p<0.05). FIG. 12 demonstrates that uninjured rats (open squares and open triangles) had scores circa 0 foot falls whether injected with HAMC or aCSF, demonstrating the safety of HAMC injection in the intrathecal space. The data suggest HAMC-treated animals having sustained SCI show statistically significant improvement in function at day 7 compared to their uninjured aCSF treated counterparts. This effect may be observed due to inherent wound-healing properties of HA, and demonstrates that HAMC on its own has intrinsic therapeutic benefit.

Figure 13:
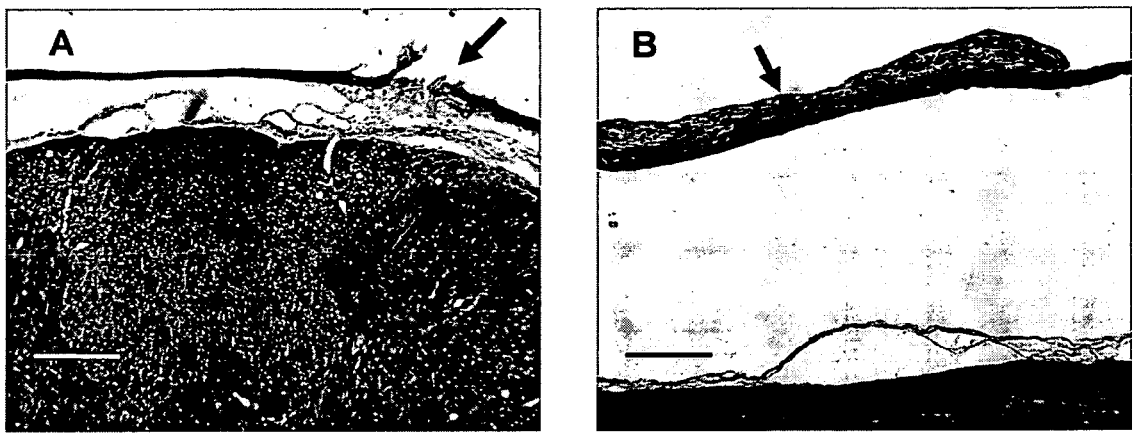
FIG. 13 provides Hematoxylin- and Eosin-stained histological sections of spinal cords injected with A) aCSF and B) HAMC, respectively.
Figure 14:
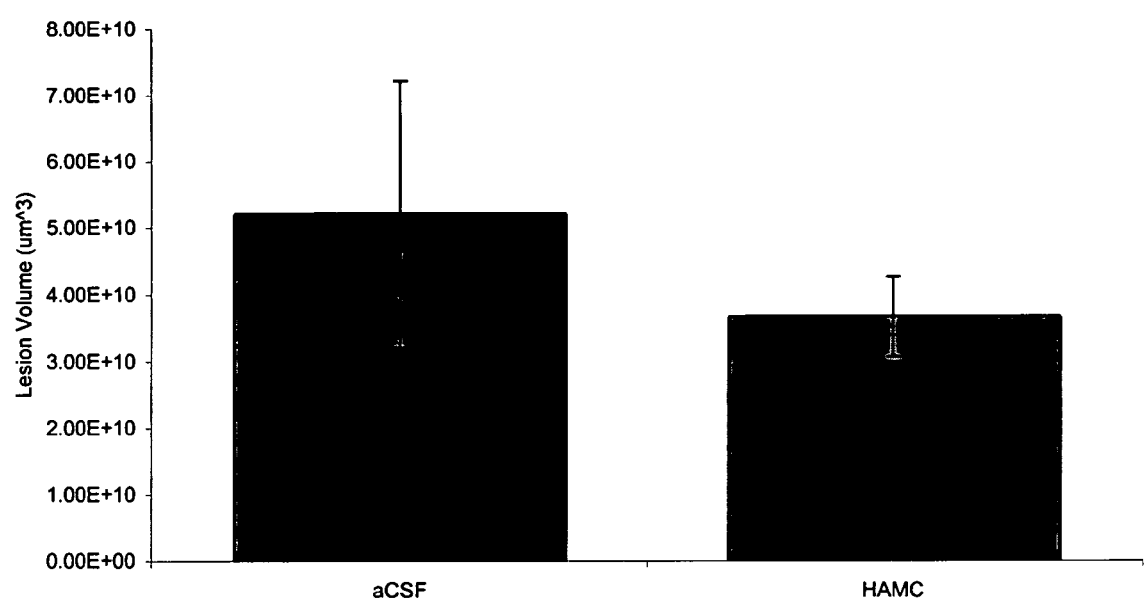
FIG. 14 is a graph of the cavitation volume in a laminectomized rat following injection with aCSF or HAMC.
Figure 15:
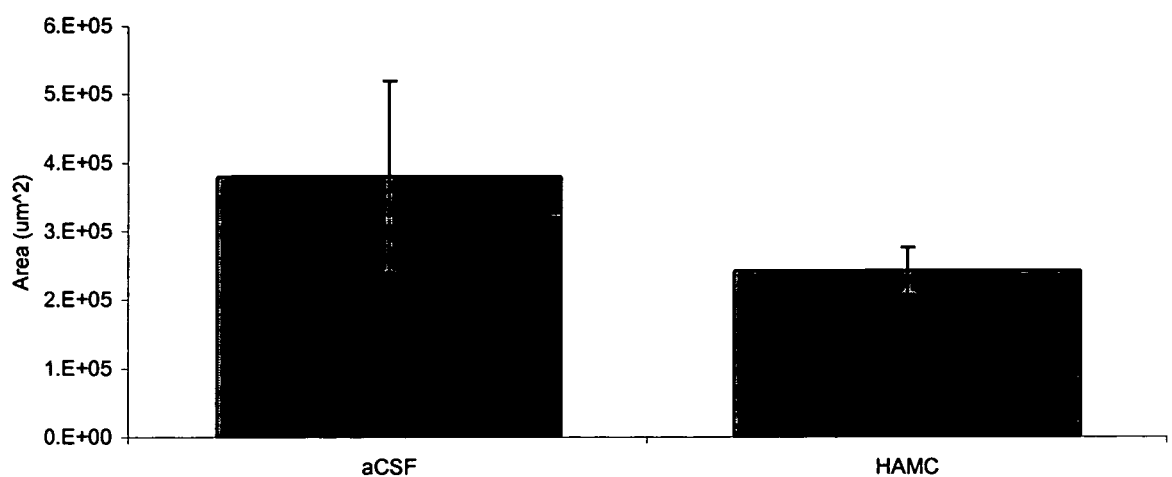
FIG. 15 is a graph of the area of inflammation in a laminectomized rat following injection with aCSF or HAMC. These values are statistically different ($p<0.05$).

Histology and immunohistochemistry analyses were conducted. Sections from injured and uninjured animals treated with HAMC or aCSF were stained with Luxol Fast Blue, hematoxylin and eosin, Mason's Trichrome, TUNEL, ED-1, and GFAP. Results from staining indicate that HAMC is biocompatible within the intrathecal space for 1 month in rats as no significant scar formation was observed within the intrathecal space. Moreover, it was observed that the puncture wound in the dura resealed after the injection of HAMC; similar results were not observed in animals injected with aCSF, FIG. 13. This demonstrates a therapeutic benefit of HAMC following intrathecal delivery.

Results of staining showed that the area of inflammation was reduced in HAMC treated animals as was the cavitation area following laminectomy, further evidence of the intrinsic therapeutic benefit of HAMC. The area of inflammation of the spinal cord was significantly decreased in animals that received the HAMC injection. The size of the cavity also showed a trend to decrease for HAMC injected animals relative to aCSF-injected animals. These data demonstrate that HAMC can be used in wound healing applications.

Example 3

Blend of 2% Hyaluronic Acid and 2% Chitosan/β-Glycerophospate Solution

Thermal gelling chitosan was produced as described by Chenite et al. Chitosan (Novamatrix, Norway) was autoclaved at 120° C. for 20 minutes. Under sterile conditions, 200 mg of chitosan was dissolved in 9 ml of 0.1 M HCl solution. 560 mg of glycerophosphate disodium salt (Sigma) was dissolved in 1 ml of dd H2O, and this solution was added drop by drop into the cold chitosan solution, resulting in a 2 w/v % thermal gelling chitosan solution. Blends of CH with HA were made similarly to the blends of MC with HA as described in Example 1. HACH is a physical blend of 2% HA dissolved in a 2 wt % CH solution.

Unlike methylcellulose, chitosan is enzymatically degradable, potentially providing further control over degradation rates and greater ranges of molecular weights that can be used. The 2% CH solution required 20 minutes of incubation at 37° C. for the gel to not flow by the inverted tube test. By blending 2% HA with the CH solution, the gelation time as determined by the inverted tube test also decreased to approximately 2 minutes, indicating that HA had the same effect on thermal gelling CH as it does on thermal gelling MC.

The disclosures of each patent, patent application and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention. The foregoing is illustrative of the present invention and is not to be construed as limiting thereof.

What is claimed is:

1. A solid gel injectable polymer matrix comprising:
   (a) methylcellulose having a molecular weight between 2,000 Da and 1,000,000 Da, and,
   (b) hyaluronic acid having a molecular weight between 100,000 Da and 7,000,000 Da;
   the polymer matrix comprising a solid gel prior to injection, undergoing shear thinning upon injection, and returning to a solid gel after injection,
   wherein the ratio of the methylcellulose to the hyaluronic acid is at least 1:1 to 20:1 w/w, and
   wherein the amounts of (a) and (b) are selected to obtain said solid gel.

2. The polymer matrix of claim 1 having a gelling temperature range of from at least 10° C. to at least 70° C.

3. The polymer matrix of claim 1 having a gelling temperature range from at least 10° C. to at least 37° C.

4. The polymer matrix of claim 1 wherein the matrix comprises 7% w/w methylcellulose and 2% w/w hyaluronic acid.

5. The polymer matrix of claim 1 wherein the ratio of the methylcellulose to the hyaluronic acid is 3.5:1 w/w.

6. The polymer matrix of claim 1 wherein the methylcellulose and the hyaluronic acid are dissolved in an aqueous solvent selected from the group comprising: water, saline, artificial cerebrospinal fluid, and buffered solutions.

7. The polymer matrix of claim 1 having an altered rate of degradation by increasing the hydrophobicity of the hyaluronic acid.

8. The polymer matrix of claim 1 having an altered rate of degradation by the addition of at least one of a thiol group and an acrylate group to the hyaluronic acid.

9. The polymer matrix of claim 1 for transdermal, oral, sub-cutaneous, intranasal, vaginal, buccal, intrathecal, epidural, ocular space, dental, intratumoral, intramuscular, intraarticular, or intravenous injectable delivery.

10. The polymer matrix of claim 1 for use in the treatment of central nervous system disorders.

11. The polymer matrix of claim 1 for dura matter repair following wounding.

12. A solid gel injectable polymer matrix pharmaceutical delivery vehicle comprising:
    (a) methylcellulose having a molecular weight between 2,000 Da and 1,000,000 Da;
    (b) hyaluronic acid having a molecular weight between 100,000 Da and 7,000,000 Da; and,
    (c) a pharmaceutical agent;
    the polymer matrix comprising a solid gel prior to injection, undergoing shear thinning upon injection, and returning to a solid gel after injection,
       wherein the ratio of the methylcellulose to the hyaluronic acid is at least 1:1 to 20:1 w/w, and
       wherein the amounts of (a) and (b) are selected to obtain said solid gel, for use as a carrier for said pharmaceutical agent.

13. The polymer matrix pharmaceutical delivery vehicle of claim 12 wherein the pharmaceutical agent is selected from the group comprising:
    anesthetics for use in caudal, epidural, inhalation, injectable, retrobulbar, and spinal applications;
    analgesics, selected from the group comprising acetaminophen, ibuprofen, fluriprofen, ketoprofen, voltaren, phenacetin and salicylamide;
    anti-inflammatories selected from the group comprising naproxen and indomethacin;
    antihistamines, selected from the group comprising chlorpheniramine maleate, phenindamine tartrate, pyrilamine maleate, doxylamine succinate, henyltoloxamine citrate, diphenhydramine hydrochloride, promethazine, brompheniramine maleate, dexbrompheniramine maleate, clemastine fumarate and triprolidine;
    antitussives selected from the group comprising dextromethorphan hydrobromide and guaifenesin;
    expectorants;
    decongestants, selected from the group comprising phenylephrine hydrochloride, phenylpropanolamine hydrochloride, pseudoephedrine hydrochloride, and ephedrine;
    antibiotics selected from the group comprising amebicides, broad and medium spectrum, fungal medications, monobactams and viral agents;
    bronchodilators selected from the group comprising theophylline, albuterol and terbutaline;
    cardiovascular preparations selected from the group comprising diltiazem, propranolol, nifedepine, clonidine, alpha adrenoceptor agonists, alpha receptor blocking agents, alpha and beta receptor blocking agents, antiotensin converting enzyme inhibitors, beta blocking agents, calcium channel blockers, and cardiac glycosides;
    central nervous system drugs selected from the group comprising thioridazine, diazepam, meclizine, ergoloid mesylates, chlorpromazine, carbidopa and levodopa;
    metal salts selected from the group comprising potassium chloride and lithium carbonate; minerals selected from the group consisting of iron, chromium, molybdenum and potassium;
    immunomodulators;
    immunosuppressives selected from the group comprising minocycline, cyclosporine A;
    thyroid preparations selected from the group comprising synthetic thyroid hormone, and thyroxine sodium;
    peptide and glycoprotein hormones and analogues selected from the group comprising human chorionic gonadotrophin (HCG), corticotrophin, human growth hormone (HGH-Somatotrophin) and erythropoietin (EPO);
    steroids and hormones selected from the group comprising ACTH, anabolics, androgen and estrogen combinations, androgens, corticoids and analgesics, estrogens, glucocorticoid, gonadotrophin, gonadotrophin releasing, hypocalcemic, menotropins, parathyroid, progesterone, progestogen, progestogen and estrogen combinations, somatostatin-like compounds, urofollitropin, vasopressin, methyl prednisolone, GM1 ganglioside, and cAMP;
    vitamins selected from the group comprising water-soluble vitamins and veterinary formulations;
    growth factors selected from the group comprising EGF, FGF2 and neurotrophin;
    peptides, peptide mimetics and other protein preparations;
    DNA; and,
    small interfering RNAs;
    with or without a pharmaceutically acceptable carrier or preservative.

14. The polymer matrix pharmaceutical delivery vehicle of claim 13 having an altered rate of degradation by cross-linking the hyaluronic acid.

15. The polymer matrix pharmaceutical delivery vehicle of claim 14 wherein the polymer matrix is reduced through the addition of at least one of a thiol group and an acrylate group to the hyaluronic acid.

16. The polymer matrix pharmaceutical delivery vehicle of claim 12 having an altered rate of degradation by increasing the hydrophobicity of the hyaluronic acid.

17. The polymer matrix pharmaceutical delivery vehicle of claim 16 wherein hydrophobicity is modified by acetic hydrazide coupling at a carboxyl group of the hyaluronic acid using standard coupling agents.

18. The polymer matrix pharmaceutical delivery vehicle of claim 12 wherein the pharmaceutical is encapsulated in a microsphere, nanoparticle or liposome.

19. The polymer matrix pharmaceutical delivery vehicle of claim 18 wherein at least one of a cationic and a cationic/anionic combination is added to prevent dispersion of the microsphere, nanoparticle or liposome from the matrix.

20. The polymer matrix pharmaceutical delivery vehicle of claim 12 wherein a charge stabilizer is added to promote an interaction between the polymer matrix and the pharmaceutical.

21. The polymer matrix pharmaceutical delivery vehicle of claim 12 wherein the pharmaceutical is covalently bonded to the hyaluronic acid.

22. The polymer matrix pharmaceutical delivery vehicle of claim 12 wherein the pharmaceutical is EPO.

23. A polymer matrix pharmaceutical delivery vehicle of claim 12 for delivery of neuroprotective, angiogenic or neuroregenerative pharmaceuticals.

24. The polymer matrix pharmaceutical delivery vehicle of claim 23 for use as a carrier for at least one growth factor capable of stimulating endogenous stem cells.

25. The polymer matrix pharmaceutical delivery vehicle of claim 24 wherein the growth factor is at least one of EGF, FGF2 and a neurotrophin.

26. A biodegradable polymer matrix pharmaceutical delivery vehicle as claimed in claim 12 wherein the polymer matrix is biodegradable and the delivery is by sustained release.

27. A pharmaceutical composition comprising as active ingredient a polymer matrix according to claim 1 for use in the treatment of dura matter wound healing.

28. A method for repairing dura matter of a subject following a traumatic event comprising one or more of a puncture wound, a tear and a break comprising contacting the dura matter of said subject with the polymer matrix according to claim 1.

29. A method for decreasing an inflammatory reaction following traumatic injury to dura matter of a subject comprising contacting the dura matter of said subject with the polymer matrix according to claim 1.

30. The method according to claim 28 wherein the polymer matrix is 7% w/w methylcellulose and 2% w/w hyaluronic acid.

31. The method according to claim 29 wherein the polymer matrix is 7% w/w methylcellulose and 2% w/w hyaluronic acid.

* * * * *